United States Patent [19]

Albert

[11] 4,255,412

[45] Mar. 10, 1981

[54] $T_3$ UPTAKE TEST EMPLOYING A PRECIPITATED NYLON SEPARATING AGENT

[75] Inventor: Anthony H. Albert, Villa Park, Calif.

[73] Assignee: Beckman Instruments, Inc., Fullerton, Calif.

[21] Appl. No.: 970,848

[22] Filed: Dec. 19, 1978

[51] Int. Cl.$^3$ ............... G01N 33/48; A61K 43/00; G01N 23/06

[52] U.S. Cl. .................... 424/1; 23/230 B; 424/12

[58] Field of Search ............ 23/230 B; 424/1, 12

[56] References Cited

U.S. PATENT DOCUMENTS

| | | | |
|---|---|---|---|
| 3,206,602 | 9/1965 | Eberle | 424/1 |
| 3,414,383 | 12/1968 | Murphy | 23/230 B |
| 3,464,798 | 9/1969 | Kilthau | 422/61 |
| 3,666,854 | 5/1972 | Eisentraut | 424/1 |
| 3,947,564 | 3/1976 | Shannon et al. | 424/1 |
| 4,018,883 | 4/1977 | Parslow | 424/1 |
| 4,070,153 | 1/1978 | Travis et al. | 424/1 |
| 4,108,974 | 8/1978 | Wegfahrt et al. | 424/1 |
| 4,115,537 | 9/1978 | Driscoll et al. | 424/1 |
| 4,158,703 | 6/1979 | Polito | 424/1 |

OTHER PUBLICATIONS

Hornby et al., Methods in Enzymology, 44:130–131, (1976).

*Primary Examiner*—Padgett Benjamin R.
*Assistant Examiner*—Christine M. Nucker
*Attorney, Agent, or Firm*—R. J. Steinmeyer; J. E. Vanderburgh; Robert S. Frieman

[57] ABSTRACT

An improved $T_3$ uptake test procedure characterized in that the separating agent employed therein comprises precipitated nylon 6, precipitated nylon 66, or mixtures thereof.

12 Claims, No Drawings

T₃ UPTAKE TEST EMPLOYING A PRECIPITATED NYLON SEPARATING AGENT

BACKGROUND OF THE INVENTION

1. Field of the Invention

This invention pertains to $T_3$ uptake test procedures and to a novel separating agent for use therein.

2. Description of the Prior Art

As early as 1939 (1), Treverrow reported that hormonal iodine compounds such as thyroxine constitute the major portion of the total serum iodine. Furthermore, these iodinated organic compounds could be distinguished from serum inorganic iodide because they are bound to serum protein. Since iodine constitutes 65 percent by weight of the thyroxine molecule, serum protein-bound iodine (PBI) was employed as an index of serum thyroxine ($T_4$). This indirect measurement of serum thyroxine was believed to be a good indicator of the thyrometabolic status of an individual (2,3,4). The normal range of PBI values was found to be 4–8 ug/100 ml; values below 4 ug/100 ml were consistent with hypothyroidism whereas values above 8 ug/100 ml were indicative of thyrotoxicosis (hyperthyroidism).

A major pitfall of the PBI test is its inherent lack of specificity since high levels of inorganic iodide, radio-opaque dyes and certain drugs give abnormally high values. In b 1964, Murphy and Pattee (5) introduced their competitive protein binding analysis (CPB) for serum thyroxine which solved most of the non-specificity problems associated with the PBI test. Due to the fact that CPB tests for serum thyroxine also required an extraction of the $T_4$ from the remainder of the serum components, recovery variability has lead to problems both in accuracy and precision.

Recently, radioimmunoassay (RIA) has become the method of choice for measuring serum thyroxine (6). The RIA technique can be run directly on serum without extraction and therefore yields a simple and yet highly specific test. In general, results from RIA are from 5 to 25 percent higher than those from CPB tests.

Although the direct measurement of serum thyroxine is not influenced by exogenous iodine, the value obtained will be influenced by the level of the circulating thyroxine binding proteins. A number of states which are totally unrelated to thyroid disease may cause abnormal serum levels of thyroxine. Changes in the serum level of circulating thyroxine binding proteins may cause the serum thyroxine level to be high or low even in the presence of normal thyroid function. Although the primary protein involved is thyroxine binding globulin (TBG), both thyroxine binding prealbumin (TBPA) and albumin also bind $T_4$. Normally $T_4$ is distributed as follows: 65% on TBG, 25% on TBPA, and 10% on albumin (7). In general, changes in the TBG concentrations correlate much better with anomalies in thyroid function tests, such as the PBI or total thyroxine than do changes in TBPA (8).

Estrogen is one of the most important factors influencing the level of TBG, its effect being most notable in individuals receiving oral contraceptives or during pregnancy. In both cases TBG concentrations are markedly elevated and consequently due to the increased binding sites, the serum $T_4$ or PBI are elevated above normal High serum thyroxine values are also found in euthyroid subjects who have increased levels of TBG (idiopathic increase of TBG) or hage hyperprotenemia. Androgens have an opposite effect to estrogens in that they lower the TBG concentration and lead to falsely low serum $T_4$ or PBI values. Other situations where the TBG concentration is below normal include an idiopathic decrease of TBG, the nephrotic syndrome and other hypoproteinimic states. Finally, a number of drugs such as diphenylhydantoin and salicylates, compete with thyroxine for binding sites on TBG, displace $T_4$ from the TBG and thus result in fasely low serum values.

Although the most accurate method to measure TBG concentrations involves the electrophoretic method of Orsorio et al. (9), the technique is too cumbersome for routine use. The method of choice which has been used for this purpose is one of the many variations of the triiodothyronine ($T_3$) uptake test. Hamolsky et al. (10) first performed this type of test and used red cells as the inert binder of $T_3$. All $T_3$ uptake tests are designed to assess the unsaturated binding capacity of serum proteins most notably TBG. The test is based on the fact that TBG binds $T_3$ less firmly than $T_4$ and therefore should not upset the equilibrium set-up between $T_4$ and TBG and, further, $T_3$ is not normally bound to TBPA.

In the $T_3$ uptake test an equilibrium is developed between the patient's serum, added labeled $T_3$ and an inert exogenous binder (separating agent) of the labeled $T_3$. One must add a sufficient amount of labeled $T_3$, e.g., $^{125}$I-labeled $T_3$, to saturate the binding sites on the TBG after which the labeled $T_3$ that is unbound is adsorbed by the separating agent and counted. Therefore, when the endogenous thyroxine level is increased, as in hyperthyroidism, serum TBG is relatively saturated and the $T_3$ uptake will be high. Conversely in the hypothyroid state where thyroxine output is low, the labeled exogenous $T_3$ will bind to the relatigely unsaturated TBG yielding a low $T_3$ uptake.

The major variations in $T_3$ uptake methodology today are centered around the chemical nature of the separating agent. Ion exchange resins (11, 12, 13) hemoglobin saturated charcoal (14), Sephadex G-25 (15), inorganic crystalline materials such as magnesium silicate and aluminum silicate (16), triiodothyronine antibody immobilized on the walls of polypropylene test tubes (17), insolubilized collodial suspension of bound serum albumin (18), and covalently bound serum albumin (19), all have been used as inert binders of labeled $T_3$.

BIBLIOGRAPHY

1. Trevorrow, V., *J. Biol. Chem.*, 127:737 (1939).
2. De Mowbray, R. R., et al., *Lancet*, 2:511 (1952).
3. Sunderman, F. W., et al., *Amer. J. Clin. Path.*, 24:885 (1954).
4. Dailey, M. E., et al., *New Engl. J. Med.*, 254 (19):907 (1956).
5. Murphy, B. E. P., et al., *J. Clin. Endocrinol.*, 24:187 (1964).
6. Chopra, I. J., *J. Clin. Endrocinol.*, 34:938 (1972).
7. Robbins, J., et al., *Hormones in Blood*, Gray, C. H., et al., eds., Academic Press, London, 2nd Ed., 1:430 and 447 (1967).
8. Thomas, J. A., et al., *Hormone Assays and Their Clinical Application*, Loraine, J. A., et al., eds, Churchill Livingston, New York, 4th Ed., Vh. 12 (1976).
9. Osorio, C., et al., *Clin. Sci.*, 21:355 (1961).
10. Hamolsky, et al., *J. Clin. Endocrinol.*, 17:33 (1957).

11. Mitchell, M. L., et al., *J. Clin. Endocrinal. Metabi,* 20:1474 (1960).
12. U.S. Pat. No. 3,414,383.
13. U.S. Pat. No. 3,206,602.
14. Herbert, J., et al., *J. Lab. & Clin. Med.,* 66 (5):814 (1965).
15. Free, A. H., et al., *Clin. Chem.,* 15:762 (1969).
16. U.S. Pat. No. 3,666,854.
17. Coleman, L. H., et al., *Clin. Chem.,* 23 (6):938 (1977).
18. MAAT—$3^{tm}$, $^{125}I$ $T_3$ *Uptake Assly. for Determination of Unsaturated TBG Binding Capacities of Serum,* Curtis Laboratories, Inc. 1948 E. $46^R$ St, Los Angeles, California 90058 (June 24, 1976).
19. Alan J. Polito, U.S. application Ser. No. 877,043, filed Feb. 13, 1978.

The above publications are incorporated herein in tot by reference.

SUMMARY OF THE INVENTION

This invention encompasses a $T_3$ uptake test procedure of the type wherein a solution is contacted with labeled $T_3$ and a separating agent. The serum bound labeled $T_3$ and the separating agent bound labeled $T_3$ are separated into two fractions and at least one of said fractions is measured. The $T_3$ uptake procedure of the instant invention is characterized in that the solution is contacted with a separating agent selected from a group comprising precipitated nylon 6, precipitated nylon 66, and mixtures thereof.

As used herein the term precipitated nylon 6 and precipitated nylon 66 denotes nylon 6 and nylon 66, respectively, that has been dissolved and brought back out of solution.

DESCRIPTION OF THE PREFERRED EMBODIMENTS

The novel separating agent within the scope of this invention is selected from a group comprising precipitated nylon 6, precipitated nylon 66, and mixtures thereof. Preferably the separating agent employed in the $T_3$ uptake test is precipitated nylon 6.

Precipitated nylon 6, precipitated nylon 66, and mixtures thereof can be employed as a separating agent in the $T_3$ uptake test procedure of the instant invention in any convenient form, e.g., as a powder, as a suspension, or in tablet form. Methods applicable to the manufacture of precipitated nylon 6, precipitated nylon 66, and mixtures thereof in powder and suspension form are disclosed herein. Methods applicable to the manufacture of precipitated nylon 6, precipitated nylon 66, and mixtures thereof in table tablet form are disclosed in Remington's Pharmaceutical Sciences, Mack Publishing Co., Pa. (1965), said publication being incorporated herein in total by reference.

The novel separating agents within the scope of this invention can be prepared according to various methods for making precipitated nylon 6 and precipitated nylon 66. See Hornby et al., *Methods in Enzymology,* 44:130–131 (1976), sub-sub section entitled "Nylon Powder", said publication being incorporated herein in toto by reference. A preferred process for making the precipitated nylon powders for use in the $T_3$ uptake test of the instant invention is to add either nylon 6 or nylon 66 with stirring to a cool calcium chloride ($CaCl_2$)-methanol solution, more preferably a 20% $CaCl_2$-methanol solution. Continue to stir and allow the resulting suspension to warm to room temperature. Stir from about 30 minutes to about 3 hours until all the nylon has dissolved. To the dissolved nylon solution add, with stirring, a volume of methanol equal to about two times the volume of methanol originally used. To the resulting solution add slowly with stirring a volume of water equal to about the original volume of methanol employed. At this point a white powder precipitates out to form a thick suspension. Collect and wash the suspension with water to remove the methanol and $CaCl_2$.

The washed precipitated nylon powder can then be suspended in water to make a stock solution. The stock solution can then be further diluted with a suitable buffer, e.g., barbital buffer, pH 8, in order to obtain $T_3$ uptake values of about 30 for normal serum.

The $T_3$ uptake test procedure of the instant invention entails contacting solutions with labeled $T_3$ and the novel separating agent of the instant invention; separating serum bound labeled $T_3$ and separating agent bound labeled $T_3$ into two fractions; and measuring at least one of said fractions via techniques well known to those skilled in the art. See Sunderman, F. W. et al., *Laboratory Diagnosis of Endocrine Diseases,* Ch. 19, Warren H. Green, Inc., St. Louis, Mo. (1971), said publication being incorporated herein in toto by reference.

In one preferred embodiment the $T_3$ uptake procedure entails a method in which continuous agitation and thereby the need to stopper the tube is eliminated. See Chan et al., *Ann. Clin. Biochem.,* 12:173 (1973), said publication being incorporated herein in toto by reference. Preferably, the $T_3$ uptake procedure of the instant invention is a radio-assay procedure which technique is well known to those skilled in the art. See Skelley et al., *Clinical Chemistry,* 19(2):146 (1973), said publication being incorporated herein in toto by reference. Any suitable radioactive label, e.g., $^{131}I$ and $^{125}I$, can be employed. The preferred label is $^{125}I$.

The following examples are provided for the purpose of further illustration only and are not intended to be limitations on the disclosed invention.

EXAMPLE 1

Preparation of 20% Calcium Chloride-Methanol Dissolving Solution

Anhydrous calcium chloride ($CaCl_2$; 40 gm) was added to anhydrous methanol (MeOH). The mixture was stirred until all the $CaCl_2$ dissolved and the stirring was continued until the solution returned to room temperature. The volume of the solution was then adjusted to 200 ml with MeOH thereby yielding a 20% $CaCl_2$-MeOH dissolving solution.

EXAMPLE 2

Preparation of Precipitated Nylon 6 Adsorbant 20% $CaCl_2$-MeOH Dissolving Solution Nylon 6 powder (10 gm) was added with stirring to 100 ml of the 20% $CaCl_2$-MeOH dissolving solution (temperature about 5°–8° C.) as prepared in Example 1. The resulting suspension was stirred and allowed to warm to room temperature. The stirring was maintained until all the nylon 6 powder was dissolved.

The solution containing the dissolved nylon 6 was then diluted with 200 ml MeOH. To the resulting solution was added, with rapid stirring, 100 ml water ($H_2O$). Stirring was maintained until all the nylon 6 precipitated.

The suspension containing the precipitated nylon 6 was then vacuum filtered and washed, while under vacuum filtration, with a copious amount of $H_2O$.

After washing, moderate vacuum filtration was continued until the majority of water was removed from the filter cake of precipitated nylon 6.

The filter cake was added to 380 ml $H_2O$ and the resulting mixture was stirred until a homogeneous suspension was obtained.

EXAMPLE 3

Preparation of Precipitated Nylon 6 Adsorbant In 88% Aqueous Phenol

Aqueous phenol (88%; 20 ml) was cooled with stirring in an ice bath until it congealed. With continued stirring, nylon 6 powder (2.5 gm) was added to the congealed aqueous phenol. Stirring was maintained while the resulting suspension was allowed to warm to room temperature and stirring was then continued until all the nylon 6 powder had dissolved.

MeOh (75 ml) was then added, with rapid stirring, to the thick solution of dissolved nylon 6. Stirring was maintained until all the nylon 6 precipitated and then continued for an additional hour. The mixture containing precipitated nylon 6 was vacuum filtered and washed under vacuum filtration with 50 ml of MeOH followed by 100 ml of $H_2O$.

After washing, moderate vacuum filtration was continued until the majority of water was removed from the filter cake of precipitated nylon 6.

The filter cake was then added to 100 ml $H_2O$ and the resulting mixture was stirred until a homogeneous suspension was obtained.

The homogeneous suspension of Examples 2 and 3 can be titered using any $T_3$ uptake procedure recognized by those skilled in the art to determine the proper dilution to be used in the $T_3$ uptake assay. These recognized procedures are analogous to the $T_3$ uptake titer procedures employed by those skilled in the art in determining the proper dilution of other adsorbants to be used in a $T_3$ uptake assay.

EXAMPLE 4

Correlation Study

Serum Samples (18) and control serum (3) were assayed for $T_3$ uptake via a $T_3$ protocol as set forth in BECKMAN® $T_3$ Uptake Reagent System for the Assessment of Unsaturated Serum Binding Capacity, Beckman Instruments, Inc., Fullerton, Calif. (February, 1977) (Beckman Instructions No. 015-555325-B) using precipitated nylon 6 powder as prepared in Example 2 as the adsorbant. The serum samples and control sera were also assayed for $T_3$ uptake via the NML Tritab Kit procedure. The data obtained from these assays are set forth in Table I.

TABLE I

| Controls | Correlation Study | |
|---|---|---|
| | Precipitated Nylon 6, ATA Ratio* | NML, ATA Ratio* |
| Beckman Control Serum | 1.055 | 0.955 |
| Lederle I | 1.147 | 1.100 |
| Lederle II | 1.405 | 1.320 |

TABLE I-continued

| Controls | Correlation Study | |
|---|---|---|
| | Precipitated Nylon 6, ATA Ratio* | NML, ATA Ratio* |
| Serum Samples | | |
| 1 | 1.123 | 1.100 |
| 2 | 0.879 | 0.865 |
| 3 | 1.053 | 1.070 |
| 4 | 1.134 | 1.110 |
| 5 | 0.697 | 0.676 |
| 6 | 0.983 | 0.928 |
| 7 | 0.852 | 0.878 |
| 8 | 0.904 | 0.863 |
| 9 | 1.066 | 1.080 |
| 10 | 1.104 | 1.170 |
| 11 | 0.880 | 0.960 |
| 12 | 0.971 | 1.110 |
| 13 | 0.831 | 1.020 |
| 14 | 1.053 | 1.160 |
| 15 | 1.538 | 1.500 |
| 16 | 0.561 | 0.626 |
| 17 | 1.006 | 1.070 |
| 18 | 1.145 | 1.100 |

Correlation of Precipitated Nylon 6(Y) to Commercial Test (X)

$r = 0.9424$
$m = 0.9920$
$b = -0.0200$
$t = 1.00$ (t .1)
$DF = 17$

*ATA Ratio = (percent uptake) (mean of the normal range)

Based upon this disclosure, many other modifications and ramifications will naturally suggest themselves to those skilled in the art of $T_3$ uptake procedures. These are intended to be comprehended as within the scope of this invention.

The embodiments of the invention in which an exclusive property or privilege is claimed are defined as follows:

1. An improved $T_3$ uptake test procedure of the type wherein:
   (a) a solution is contacted with labeled $T_3$ and a separating agent;
   (b) serum bound labeled $T_3$ and separating agent bound labeled $T_3$ are separated into two fractions;
   (c) at least one of said fractions is measured; wherein the improvement comprises contacting said solution with a separating agent selected from a group consisting of precipitated nylon 6, precipitated nylon 66, and mixtures thereof.

2. The method of claim 1 wherein said separating agent is precipitated nylon 6.

3. The method of claim 1 wherein said separating agent is precipitated nylon 66.

4. The method of claim 1 wherein said separating agent is in powder form.

5. The method of claim 2 wherein said separating agent is in powder form.

6. The method of claim 3 wherein said separating agent is in powder form.

7. The method of claim 1 wherein said separating agent is in suspension form.

8. The method of claim 2 wherein said separating agent is in suspension form.

9. The method of claim 3 wherein said separating agent is in suspension form.

10. The method of claim 1 wherein said separating agent is in tablet form.

11. The method of claim 2 wherein said separating agent is in tablet form.

12. The method of claim 3 wherein said separating agent is in tablet form.

* * * * *